(12) United States Patent
Piponi (10) Patent No.: US 10,594,931 B2
(45) Date of Patent: Mar. 17, 2020

(54) REDUCING SMOKE OCCLUSION IN IMAGES FROM SURGICAL SYSTEMS

(71) Applicant: Verily Life Sciences LLC, South San Francisco, CA (US)

(72) Inventor: Daniele Piponi, Oakland, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 0 days.

(21) Appl. No.: 16/214,862

(22) Filed: Dec. 10, 2018

(65) Prior Publication Data

US 2019/0182421 A1 Jun. 13, 2019

Related U.S. Application Data

(60) Provisional application No. 62/597,685, filed on Dec. 12, 2017.

(51) Int. Cl.
*A61B 34/30* (2016.01)
*H04N 5/232* (2006.01)
(Continued)

(52) U.S. Cl.
CPC ....... *H04N 5/23229* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS

2009/0196476 A1 8/2009 Inoue
2012/0316421 A1 12/2012 Kumar et al.
(Continued)

FOREIGN PATENT DOCUMENTS

WO 2012/112866 A1 8/2012

OTHER PUBLICATIONS

International Search Report and Written Opinion from the International Searching Authority dated Mar. 7, 2019 for International Application No. PCT/US2018/065027, filed Dec. 11, 2018, 17 pages.

(Continued)

*Primary Examiner* — Eileen M Adams
(74) *Attorney, Agent, or Firm* — Christensen O'Connor Johnson Kindness PLLC (57) ABSTRACT

A system for improving imaging during a surgical procedure includes an image sensor coupled to a controller. The image sensor is coupled to capture a video, including a first image frame with a smoke occlusion due to surgical smoke, of the surgical procedure. The first image frame includes a plurality of pixels each having an imaged color representing a view of the tissue affected by the smoke occlusion. The controller stores instructions that when executed causes the system to perform operations. The operations include determining an estimated true color of each of the plurality of pixels. The estimated true color is closer to an unoccluded color of the tissue than the imaged color. The operations also include generating, in response to determining the estimated true color, a desmoked first image frame with a reduced amount of the smoke occlusion relative to the first image frame.

22 Claims, 6 Drawing Sheets

(51) Int. Cl.
*H04N 9/04* (2006.01)
*H04N 1/60* (2006.01)
*H04N 1/62* (2006.01)
*A61B 1/00* (2006.01)
*A61B 18/00* (2006.01)
*A61B 1/04* (2006.01)
*A61B 90/00* (2016.01)
*G06T 5/00* (2006.01)
*A61B 17/00* (2006.01)

(52) U.S. Cl.
CPC .............. *A61B 1/04* (2013.01); *A61B 18/00* (2013.01); *A61B 34/30* (2016.02); *A61B 90/361* (2016.02); *G06T 5/001* (2013.01); *H04N 1/6019* (2013.01); *H04N 1/62* (2013.01); *H04N 9/04513* (2018.08); *A61B 2017/00221* (2013.01); *A61B 2018/00595* (2013.01); *A61B 2018/00684* (2013.01); *A61B 2090/373* (2016.02); *G06T 2207/10024* (2013.01); *G06T 2207/20076* (2013.01); *G06T 2207/30004* (2013.01)

(56) References Cited

U.S. PATENT DOCUMENTS

| | | |
|---|---|---|
| 2016/0106934 A1 | 4/2016 | Hiraga et al. |
| 2016/0239967 A1* | 8/2016 | Chou .................. G06T 7/11 |
| 2016/0321785 A1 | 11/2016 | Nishimura |
| 2019/0066336 A1* | 2/2019 | Golde .................. G06T 7/90 |

OTHER PUBLICATIONS

Luo et al., "Vision-Based Surgical Field Defogging," IEEE Transactions on Medical Imaging, vol. 36, No. 10, Oct. 2017, pp. 2021-2030.

Nishino et al., "Bayesian Defogging," Int. J. Comput. Vis., 2012, vol. 98, pp. 263-278.

Tchaka et al., "Chromaticity Based Smoke Removal in Endoscopic Images," Medical Imaging 2017: Image Processing, Proceedings of SPIE, vol. 10133, 10 pages.

Photoshop Lightroom Classic CC, "Remove Haze with Dehaze Feature in Lightroom", retrieved from internet < https://helpx.adobe.com/lightroom/how-to-remove-haze-dehaze.html> on Oct. 22, 2017, 4 pages.

* cited by examiner

REDUCING SMOKE OCCLUSION IN IMAGES FROM SURGICAL SYSTEMS

CROSS-REFERENCE TO RELATED APPLICATIONS

This application claims the benefit of U.S. Provisional Application No. 62/597,685, filed Dec. 12, 2017, which is hereby incorporated by reference in its entirety.

TECHNICAL FIELD

This disclosure relates generally to imaging systems, and in particular but not exclusively, relates to image processing of images from surgical systems.

BACKGROUND INFORMATION

In recent years, computer-assisted surgery has become a popular way to overcome limitations of existing surgical procedures, and possibly enhance the capabilities of doctors performing the surgery. For example, without computerized equipment, doctors may be limited to where they can operate/examine due to the size of their hands and limited dexterity with tools. This inhibits the ability of doctors to operate on small or deep internal tissues.

In open surgery, for example, computer-guided instruments can replace traditional (hand-held) tools to perform operations such as rib spreading due to the smoother feedback assisted motions of computer-guided instruments. Robotic systems like this have been shown to reduce or eliminate tissue trauma commonly associated with invasive surgery. Moreover, these instruments may prevent surgeons from making accidental mistakes while operating.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and a method for reducing smoke occlusion in images from surgical systems are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "selecting", "identifying", "capturing", "adjusting", "analyzing", "determining", "estimating", "generating", "comparing", "modifying", "receiving", "providing", "displaying", "interpolating", "outputting", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such as information storage, transmission, or display devices.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, embodiments of the present disclosure are not described with reference to any particular programming language. It will be appreciated that a variety of programming languages may be used to implement the teachings of the disclosure as described herein.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Cauterization is a surgical technique of burning tissue to cut through, remove, or seal tissue while mitigating bleeding and damage. Cauterization devices such as an electrocautery knife, a harmonic scalpel, a laser scalpel, and the like allow a surgeon to perform cauterization at precise locations during a surgical procedure. However, surgical smoke may be released as a by-product of burning the tissue desired to be cut, sealed, or removed. In general, surgical smoke may be described as a gaseous by-product produced by electrosurgery, laser tissue ablation, ultrasonic scalpel dissection, high speed drilling or burring, or any procedure done by means of a surgical instrument that is used to ablate, cut, coagulate, desiccate, fulgurate, or vaporize tissue.

During certain situations, the surgical smoke may cause a smoke occlusion that obstructs a surgeon's view of the surgical site and potentially prevents further progress of the surgical procedure until the smoke occlusion is reduced or removed. One way of reducing the surgical smoke causing the smoke occlusion is to periodically release or evacuate the surgical smoke from the surgical site. For example, during laparoscopic surgery small incisions are made within the abdomen to allow for the insertion of surgical instruments such as an endoscope and a cutting instrument (e.g., a harmonic scalpel). The abdomen is then sealed and filled with carbon dioxide to elevate the abdominal wall above the internal organs to create a working and viewing spacing. The use of the cutting instrument may generate surgical smoke within the sealed abdominal cavity, which may create a smoke occlusion that interferes with the surgeon's view of the surgical site. Periodically, the surgeon may halt progress of the surgical procedure to have surgical staff physically evacuate the surgical site of surgical smoke with a vacuum or the like and then refill the surgical site with carbon dioxide. However, in some situations, it may not be ideal to interrupt, distract, or otherwise disrupt the surgeon from performing the surgical procedure. Moreover, there may be time critical periods in which pausing the surgical procedure is not an option.

Described herein, are embodiments of a system and a method for reducing smoke occlusion in images from surgical systems. The described embodiments can be both an alternative and/or complementary approach to physically evacuating surgical smoke from a surgical site. In particular, the described embodiments utilize image processing to reduce or remove the appearance of the smoke occlusion caused by the surgical smoke in images/videos of the surgical procedure in real-time.

Figure 1A:
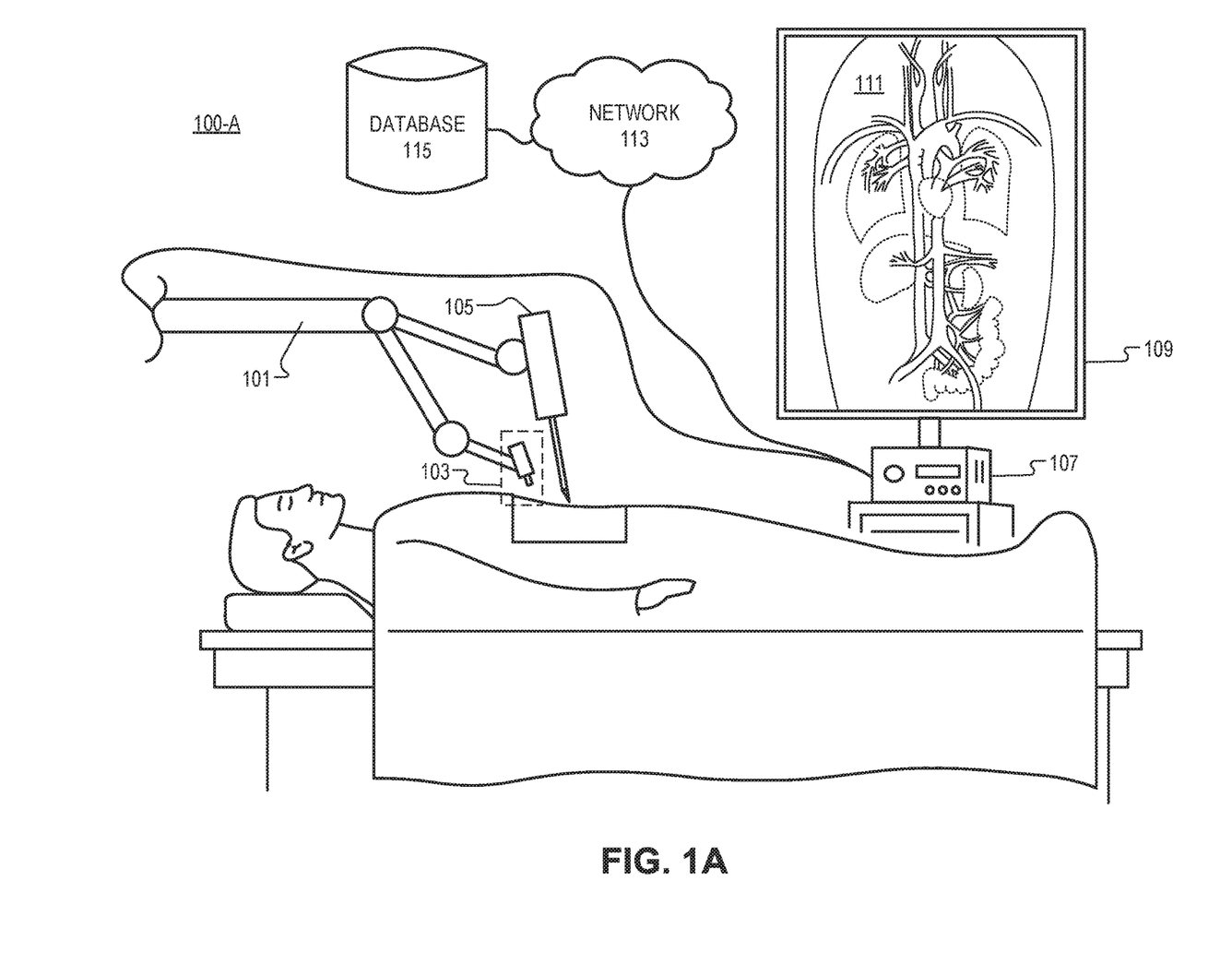
FIG. 1A is an example surgical system for outputting images with reduced smoke occlusion, in accordance with an embodiment of the disclosure.

FIG. 1A is an example surgical system 100-A that outputs images with reduced smoke occlusion that is caused by surgical smoke, in accordance with an embodiment of the disclosure. Surgical system 100-A includes a surgical robot 101, an image sensor 103 (e.g. a video camera), a surgical instrument 105 (e.g., a cauterizing instrument, such as an electrocautery knife, a harmonic scalpel, a laser scalpel, or any other surgical instrument that may cause surgical smoke to be released upon use), a controller 107 (e.g., a computer system which may, in some embodiments, include a processor and memory/storage), a display screen 109 (displaying a desmoked first image frame 111 of a surgical site that has been processed, in real-time, to have a reduced amount of a smoke occlusion caused by surgical smoke), and a database 115 (coupled to computer 107 wired or wirelessly via a network 113).

Image sensor 103 is positioned to capture a video of a surgical procedure being performed with surgical system 100-A. The video captured during the surgical procedure by image sensor 103 includes a first image frame representing a view of the surgical site and includes tissue that is at least partially occluded by a smoke occlusion due to surgical smoke. The surgical smoke may be a by-product produced during a use or activation of surgical instrument 105 (e.g., cauterization of tissue with a harmonic scalpel during a cauterization event). In particular, the first image frame includes a plurality of pixels each having an imaged color captured by image sensor 103. The imaged color representing a view of tissue affected or otherwise obstructed, at least partially, by the smoke occlusion.

Controller 107 is coupled to image sensor 103 to receive the video, including the first image frame. Controller 107 may be a computer system (e.g. one or more processors coupled to memory), an application specific integrated circuit (ASIC), a field-programmable gate array, or the like to choreograph and control, at least in part, operations of surgical system 100-A. Stored on controller 107 (e.g., on the memory coupled to controller 107 or as application specific logic and associated circuitry) are instructions, that when executed by controller 107 causes surgical system 100-A to perform operations. The operations include determining an estimated true color of each of the plurality of pixels in the first image frame based, at least in part, on the imaged color. The estimated true color is closer to an unoccluded color of the tissue than the imaged color. In other words, the estimated true color adjusts a color value of the imaged color to be closer in value to that of a true color of the tissue (e.g., the actual color of the tissue when unoccluded by the smoke occlusion). A desmoked first image frame 111 with a reduced amount of the smoke occlusion relative to the first frame is then generated, at least in part, by controller 107 based on the determined estimated true color of each of the plurality of pixels. This process may continue for each image frame of the video (e.g., the video may include a plurality of image frames, including the first image frame) to generate a desmoked video (including the desmoked first image frame 111) that is subsequently output to display screen 109 in real-time. Thus, while capturing the video of the surgical procedure, controller 107 may continuously and in real-time desmoke (e.g., reduce or remove the smoke occlusion due to the surgical smoke) the video to generate the desmoked video and subsequently output the desmoked video to display screen 109. This may allow the surgeon to perform a surgical procedure (e.g. endoscopic surgery) with less pauses or halts since it may not be necessary to physically evacuate surgical smoke as frequently, if at all. Moreover, the generation of the desmoked video in real-time may allow the surgeon to more clearly view the tissue while performing a surgical technique that generates the surgical smoke as a by-product.

In the depicted embodiment, image sensor 103 is directly coupled (wired) to controller 107, but in other embodiments, there may be intervening pieces of circuitry and controller 107 may be indirectly coupled (wireless) to image sensor 103. Similarly, in some embodiments, controller 107 may be part of a distributed system (e.g., many processors and memory units may be used in the calculations to handle processing). Additionally, database 115 is illustrated as directly coupled (wired) to controller 107 through network 113. However, it is appreciated that in some embodiments, controller 107 may be indirectly coupled (wireless) to network 113 and/or database 115. Database 115 may be a surgical video database coupled to controller 107.

The surgical video database includes a plurality of smoke-free images representing the surgical procedure without the smoke occlusion at a substantially similar anatomic location as the first image frame. For example, in some embodiments, the surgical procedure may be a cholecystectomy, during which, the surgeon's view of the gallbladder may be obstructed, at least partially, by the smoke occlusion from the surgical smoke. The plurality of smoke free-images included in the surgical video database 115 may represent a similar view of the gallbladder (of either the same or a different patient) as the view provided by image sensor 103 being outputted to display 109 (e.g., as the video that includes the first image frame). Surgical video database 115 may also be utilized to store the video for later reference or for inclusion in the calculations for reducing or removing the smoke occlusion in future image frames of the surgical procedure.

As illustrated, only a portion of surgical robot 101 is shown (e.g., there may be other parts disposed off the page). Surgical robot 101 is shown as having two arms, each respectively holding image sensor 103 and surgical instrument 105. However, in other embodiments, surgical robot 101 may have any number of arms with a variety of surgical instruments (e.g., clamps, tweezers, etc.). As shown, the arms may have a number of joints with multiple degrees of freedom so that surgical system 100-A can move freely with as many, or more, degrees of freedom as the surgeon. Additionally, surgical robot 101 may provide haptic feedback to the surgeon by way of pressure, strain, and/or stress sensors disposed within the arms or surgical instruments of surgical robot 101. Furthermore, a plurality of image sensors 103 may be utilized to form the video and corresponding plurality of image frames. Individual images captured by the plurality of image sensors 103 may be stitched together or the like by surgical system 100-A in order to seamlessly generate each of the plurality of image frames from two or more image sensors.

Figure 1B:
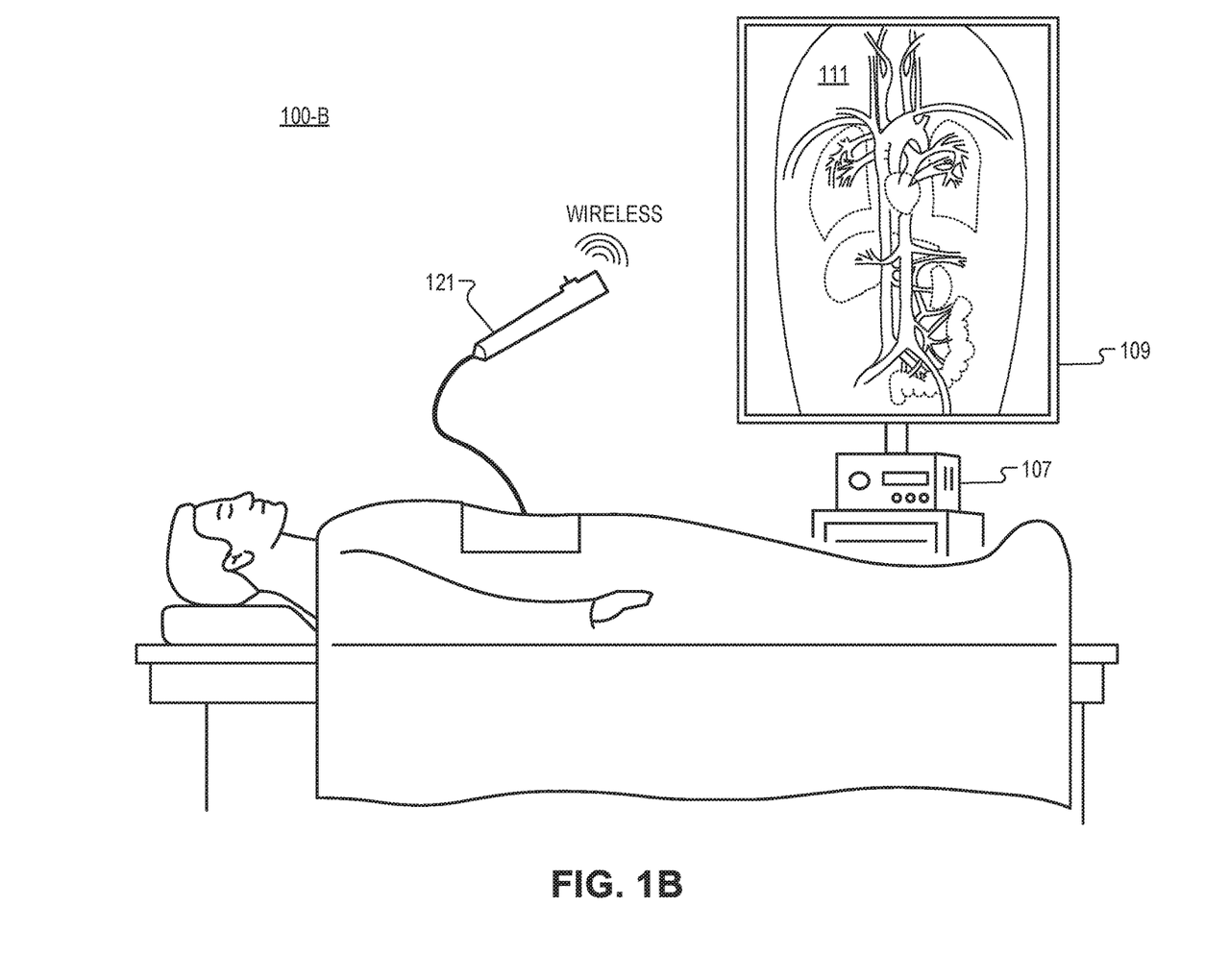
FIG. 1B is an example surgical system for outputting images with reduced smoke occlusion, in accordance with an embodiment of the disclosure.

FIG. 1B is an example surgical system 100-B for outputting images with reduced smoke occlusion, in accordance with an embodiment of the disclosure. Surgical system 100-B is similar in many respects to surgical system 100-A in FIG. 1A. However, one difference is that an endoscope 107 (e.g., a laparoscope, a bronchoscope, a cystoscope, a colonoscope, a sigmoidoscope, a thoracoscope, a laryngoscope, an angioscope, an arthroscope, or the like) is used instead of the surgical robot to capture the video of the surgical procedure. Moreover, endoscope 121 may wirelessly transfer the video (including the first image frame) to controller 107 in real-time. Endoscope 121 may be inserted into the patient (as shown) through small incisions to view and operate on the internal organs or vessels of the patient (e.g., to view the anatomical location and/or perform the surgical procedure). Surgical system 100-B illustrates the output to display screen 109 the desmoked first image frame 111. Furthermore, it is appreciated that surgical system 100-B illustrates the systems and methods disclosed herein are compatible with a variety of surgical procedures and surgical instruments, as one of ordinary skill in the art will appreciate.

Figure 2:
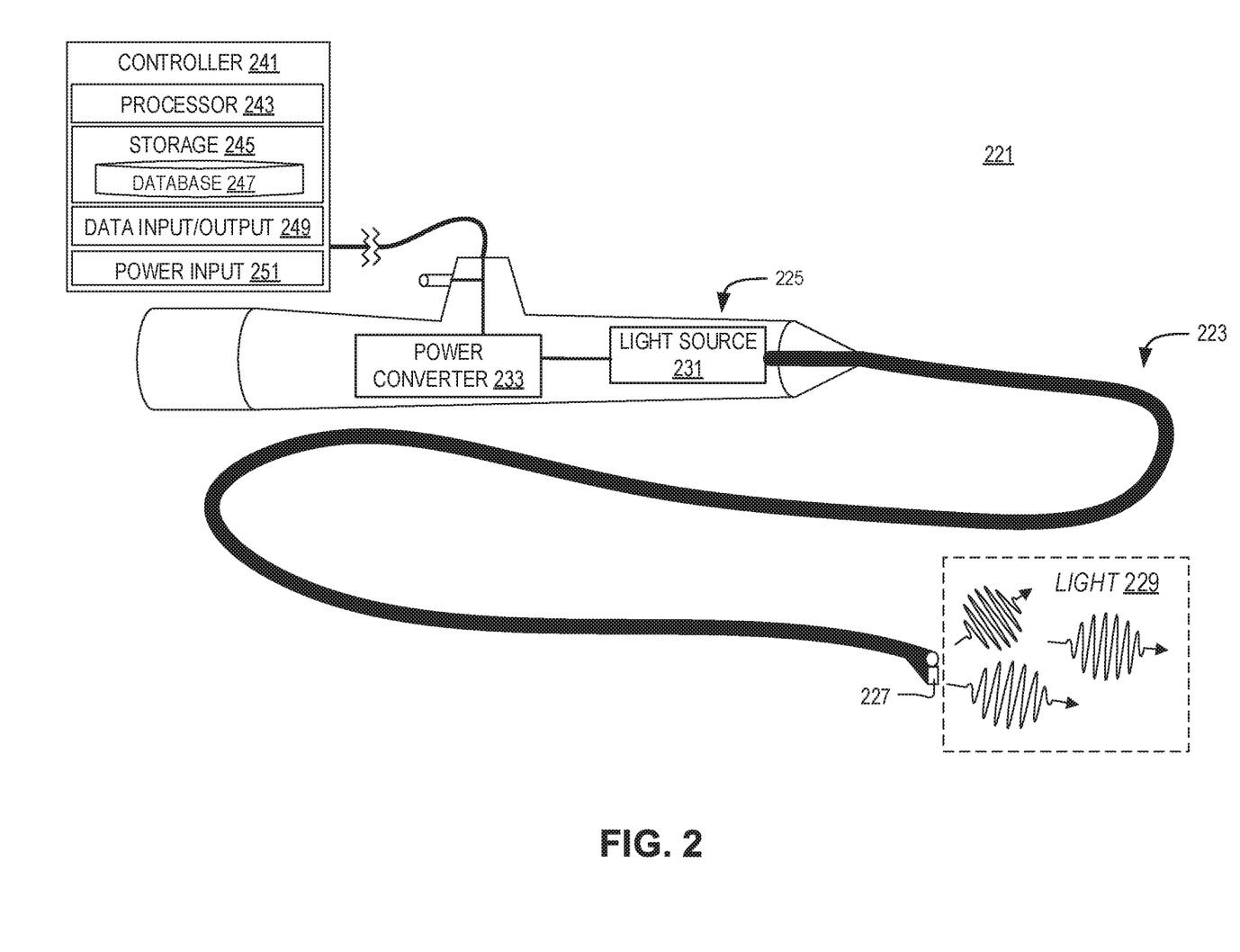
FIG. 2 is an example endoscope which may be used in the surgical system of FIG. 1B, in accordance with an embodiment of the disclosure.

FIG. 2 is an example endoscope 221 which may be used in the surgical system of FIG. 1B, in accordance with an embodiment of the disclosure. Endoscope 221 is one possible implementation of endoscope 121 of FIG. 1B. Referring back to FIG. 2, endoscope 221 includes a fiber optic cable 223, a housing 225, an image sensor 227, a light source 231, and a power converter 233.

Endoscope 221 includes a proximal end (to be hand-held or mounted) and a distal end (end of fiber optic cable 223 closest to image sensor 227) to be inserted into a patient receiving the surgical procedure. Light source 231 is optically coupled to the proximal end of fiber optic cable 223 to emit visible light 229 into fiber optic cable 223 for output from the distal end. The distal end is positioned within the patient and illuminates the surgical site. Image sensor 227 is coupled to the distal end of fiber optic cable 223 and positioned to receive a reflection of visible light 229 that illuminates the surgical site to capture the video (including the first image frame) of the surgical procedure.

Controller 241 is similar in many regards to controller 107 of the surgical system of FIG. 1A and may include at least the same components and functionality. Referring back to FIG. 2, controller 241 may be disposed internal (e.g. disposed with housing 225) or external (e.g. wired or wirelessly connected) to endoscope 221. Controller 241 includes a processor 243, storage 245 (e.g., any computer-readable storage medium) with database 247, data input/output 249 (e.g., to send/receive the video from image sensor 227), and power input 251 (e.g., to power endoscope 221). Data input/output 249 may include an input apparatus coupled to controller 241. The input apparatus may be positioned to receive an input command from an operator (e.g. the surgeon). In response to receiving the input command, the surgical system may adjust a level of the reduced amount of the smoke occlusion relative to the first image frame. In other words, the surgeon may manual adjust the amount of the smoke occlusion that is reduced or removed. In some embodiments, a linear interpolation of the plurality of image frames compared to the desmoked plurality of image frames may be utilized to adjust the amount the smoke occlusion is reduced or removed. For example, linear interpolation of the first image frame and the desmoked first image frame may allow for controlling the amount of the smoke occlusion.

Figure 3:
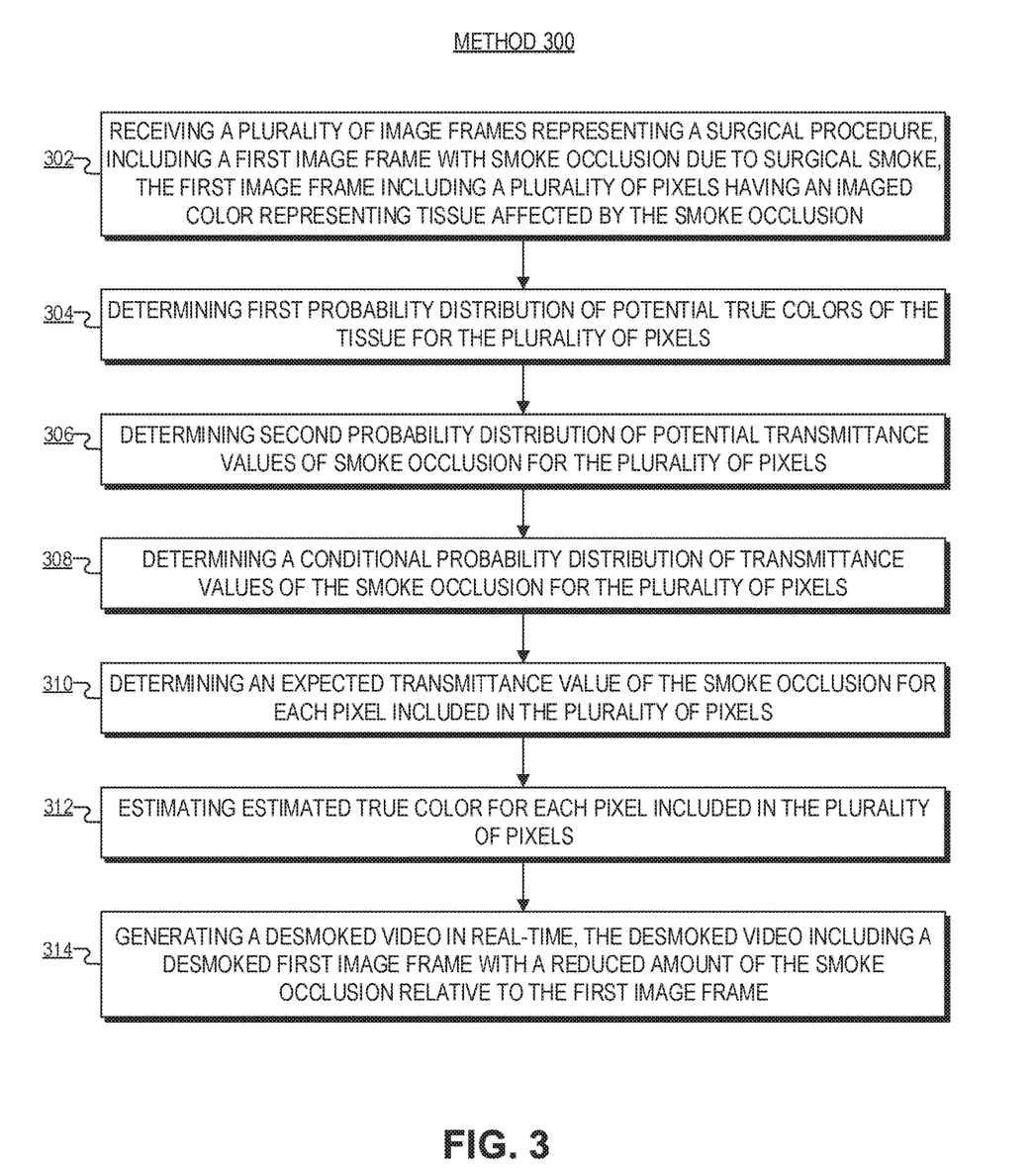
FIG. 3 is a flow-chart describing a method of reducing smoke occlusion in images from surgical systems, in accordance with an embodiment of the disclosure.

FIG. 3 is a flow-chart describing method 300 of reducing the smoke occlusion in images (e.g., the video of the surgical procedure, including the first image frame) from surgical systems (e.g., surgical system 100-A of FIG. 1A and surgical system 100-B of FIG. 1B), in accordance with an embodiment of the disclosure. Method 300 may be implemented by various hardware elements, including, but not limited to the embodiments of surgical system 100-A of FIG. 1A and surgical system 100-B of FIG. 1B. In particular, a controller (e.g., controller 107 of FIG. 1A, controller 107 of FIG. 1B, or controller 241 of FIG. 2) may include instructions (e.g., stored on memory) or logic (e.g. an application specific integrated circuit) for performing method 300. Additionally, or alternatively, method 300 may be implemented as instructions stored on any form of a non-transitory machine-readable storage medium.

Referring back to FIG. 3, method 300 describes a technique for improving imaging during the surgical procedure in real-time by reducing an amount of smoke occlusion due to surgical smoke. Additionally, method 300 may be utilized on smoke-occluded surgical videos for post-operative analysis. Surgical smoke generated by the surgical procedure is typically a white color and may cause a smoke occlusion that at least partially obstructs the surgeon's view of the surgical site. The surgical smoke color is substantially different than the unoccluded color (e.g., the actual color or true color) of the tissue, which generally has a large red color component due to the vasculature nature of the tissue. Method 300 looks at the imaged color of individual pixels (e.g., each of the plurality of pixels included in the first image frame of the video) and estimates a probability distribution for how much of the surgical smoke is occluding (e.g. the smoke occlusion) the view of any particular one of the individual pixels. Subsequently, the contribution of the smoke occlusion to the imaged color for each of the plurality of pixels can be reduced or otherwise removed to generate a desmoked image (e.g., the desmoked video including the desmoked image frame).

Block 302 shows receiving a plurality of image frames representing a surgical procedure. The plurality of image frames includes a first image frame with smoke occlusion caused by surgical smoke. The first image frame includes a plurality of pixels, each having an imaged color representing a view of the tissue affected by the smoke occlusion. The plurality of image frames may be included in a video captured by an image sensor. The imaged color of each of the plurality of pixels is representative of a color value determined or sensed, at least in part, by the image sensor.

As described in the various embodiments of the disclosure, the color value of the imaged color, the tissue, and the surgical smoke may be defined in a variety of ways. For example, the color value of each of the plurality of pixels may be defined by components in the RGB color space with a certain amount of precision. In the illustrated embodiments, eight-bit precision is utilized which allows for R (red), G (green), and B (blue) component values between zero and two hundred and fifty five. For example, an endoscope having images with eight-bit precision per channel may be utilized, in some embodiments. Additionally, it is assumed that a simple linear mixing model applies to how the color value of the imaged color is affected by the smoke occlusion, and that the color values of the plurality of image frames have a linear representation of intensities. Therefore, the imaged color is based on a combination of the color value of the smoke occlusion, a transmittance value of the smoke occlusion/surgical smoke, and the actual/true color value of the tissue that is unaffected by the smoke occlusion. Furthermore, it is appreciated that the chosen color space and level of precision of the present disclosure should not be deemed limiting and that any possible combination of color space and level of precision may be utilized, as known by one of ordinary skill in the art.

In some embodiments, it is appreciated that the color value for each of the plurality of image frames received may not necessarily have a linear representation of intensities. For example, an imaging processing pipeline (e.g., from an endoscope) may apply an adjustment (e.g., a gamma correction) to the color value of the pixels included in the plurality of image frames. Thus, in certain situations, it may be desirable to obtain the unadjusted color value of the pixels in the plurality of image frames before reducing the amount of the smoke occlusion. After the reduction of the smoke occlusion, the adjustments to the image color may be re-applied. In other situations, it is appreciated that it may not be necessary to obtain the unadjusted image color before reducing the amount of the smoke occlusion.

Block 304 illustrates determining a first probability distribution of potential true colors of the tissue for the plurality of pixels. The first probability distribution may be determined, at least in part, from a plurality of smoke-free images representing the surgical procedure without the smoke occlusion at a substantially similar anatomical location as the first image frame. Thus, the plurality of image frames and the plurality of smoke-free images both correspond to a similar view (e.g., of the same organs). In other words, the first probability distribution represents the color probability of a randomly picked pixel that represents a view of the tissue unaffected by the smoke occlusion. The plurality of smoke-free images may be received from smoke-free videos in a surgical video database (e.g. database 115 of surgical system 100-A in FIG. 1A or database 247 coupled to endoscope 221 of FIG. 2).

Block 306 shows determining a second probability distribution of potential transmittance values of the smoke occlusion for the plurality of pixels. In some embodiments, the second probability distribution is determined, or otherwise assumed, to be based off a uniform distribution of a smoke probability density function (e.g., one). In other embodiments, the second probability distribution is determined from smoke-occluded video that is affected by the smoke occlusion/surgical smoke. For example, telemetry data may be collected when capturing smoke-occluded video. Smoke occluded image frames included in the smoke-occluded video may be annotated when the surgical instrument (e.g. a harmonic scalpel) is used, which generates the smoke occlusion from the surgical smoke. Accordingly, the second probability distribution may be determined from the smoke occluded image frames.

Block 308 illustrates determining a conditional probability distribution of transmittance values of the smoke occlusion for the plurality of pixels. The conditional probability distribution may utilize Bayes' theorem/Bayesian inference and be based, at least in part, on the imaged color, the first probability distribution of the potential true colors of the tissue, and the second probability distribution of the potential transmittance values of the smoke occlusion.

In some embodiments, an activation of a cauterizing instrument (e.g., harmonic scalpel) is monitored to detect a cauterization event that generates surgical smoke as the by-production. In response to detecting the cauterization event, the conditional probability distribution of the transmittance values of the smoke occlusion may be adjusted to compensate for an increased likelihood the smoke occlusion is affected the imaged color. For example, the second probability distribution of the potential transmittance values of the smoke occlusion may be weighted towards a high probability that the smoke occlusion/surgical smoke is present. Similarly, in the same or other embodiments, in response to receiving an input command from an input apparatus, the second probability distribution of the potential transmittance values may be adjusted to adjust a level of the reduced amount of the smoke occlusion relative to the first image frame. This may allow the surgeon to control the amount of smoke occlusion reduction.

The conditional probability distribution of the transmittance values of the smoke occlusion for the plurality of pixels is based on a central assumption that:

$$S(x) = tC(x) + (1-t)A \qquad (1)$$

where $S(x)=(S_r(x), S_g(x), S_b(x))$, which corresponds to the red, green, and blue color components of the imaged color in RGB color space, t corresponds to the transmittance value of the smoke occlusion from the surgical smoke, $C(x)=(C_r(x), C_g(x), C_b(x))$, which corresponds to the red, green, and blue color components of the estimated true color of the tissue if the smoke occlusion were absent, and $A=(A_r, A_g, A_b)$, which corresponds to the red, green, and blue color components of the smoke occlusion if the surgical smoke is dense enough to be completely opaque, referred herein as the airlight color. The airlight color A is a fixed color value that may be determined experimentally, from one or more smoke-occluded videos, or based off an assumed or expected smoke color. In some embodiments, the airlight color A is determined to have a color value representing a white color. This is because it is assumed that white regions are unusual in much of the human anatomy, so the pixels included in the plurality of image frames of the surgical procedure (with the surgical instruments removed from the plurality of image frames) that are closest to white are likely the color of the smoke occlusion.

Thus, if A and t are known, the estimated true color can be estimated by re-arranging Equation (1) to determine C(x) as follows:

$$C(x)=(S(x)-(1-t)A)/t \qquad (2)$$

This central assumption presented in Equation 1 makes sense because when the transmittance value t of the smoke occlusion is zero, the surgical smoke is opaque and the imaged color S(x) simply corresponds to the airlight color. Similarly, when the transmittance value t of the smoke occlusion is one, the imaged color S(x) corresponds to the estimated true color value of the tissue if the smoke occlusion were absent. Therefore, based on Equation 2 method 300 aims to recover C(x) to determine the estimated true color of the tissue given the imaged color S(x). However, Equation 2 is an underconstrained or undetermined system since the estimated true color C(x) may not be able to be recovered without some other a priori information. This is where the first probability distribution, the second probability distribution, and the imaged color S(x) are utilized, in conjunction with Bayes' theorem, to generate the conditional probability distribution as a solution to the undetermined system.

Assuming independence of the transmittance values t of the smoke occlusion from the imaged color S(x), Equation 2 in combination with Bayes' theorem can be used to compute the conditional probability distribution of the transmittance values t of the smoke occlusion given the imaged color S(x) is observed:

$$\frac{q(t)p((S_r-(1-t)A_r)/t, (S_g-(1-t)A_g)/t, (S_b-(1-t)A_b)/t)}{\int q(t)p((S_r-(1-t)A_r)/t, (S_g-(1-t)A_g)/t, (S_b-(1-t)A_b)/t)dt} \qquad (3)$$

where p(r,g,b) is the first probability distribution of the potential true colors of the tissue, given an imaged color S(x) has been observed, and q(t) is the second probability distribution of potential transmittance values of the smoke occlusion.

Block 310 shows determining an expected transmittance value of the smoke occlusion for each pixel included in the plurality of pixels. One way of determining the expected transmittance value is to adjust the numerator of Equation 3 by multiplying the function by t and then integrating over all values of the transmittance values t, which yields:

$$\frac{\int tq(t)p((S_r-(1-t)A_r)/t, S_g-(1-t)A_g)/t, (S_b-(1-t)A_b)/t)dt}{\int q(t)p((S_r-(1-t)A_r)/t, (S_g-(1-t)A_g)/t, (S_b-(1-t)A_b)/t)dt}. \qquad (4)$$

In other words, Bayes' theorem is used to estimate the expected transmittance value by integrating over all values of the potential transmittance values t, weighted by the a priori likelihood of t given by the second probability distribution of potential transmittance values of the smoke occlusion q(t). Standard techniques such as numerical integration may be used to solve for the expected transmittance value. Alternatively, other approaches, such as a max-likelihood estimator for the transmittance values t of the smoke occlusion may also be used in other embodiments.

Block 312 illustrates estimating the estimated true color for each pixel included in the plurality of pixels. Once the expected transmittance value of the smoke occlusion is determined for each of the plurality of pixels based, at least in part, on the conditional probability distribution, the estimated true color value may be estimated. This can be done by inputting the expected transmittance value and the imaged color for each of the plurality of pixels and computing the estimated true color C(x) with Equation 2.

Block 314 shows generating a desmoked video in real-time, the desmoked video including the desmoked first image frame with a reduced amount of the smoke occlusion relative to the first image frame. The desmoked first image frame is generated by replacing the color value of the imaged color from the first image frame with the estimated true color for each of the plurality of pixels. Similarly, this process may be completed for each image frame included in the plurality of image frames that form the video in order to generate the desmoked video.

In some embodiments, the task of determining the estimated true color for each of the plurality of pixels may be too computationally costly for the surgical system to generate the desmoked video in real-time. However, the surgical system may off-load some of the computations by generating a look-up table of pre-computed estimated true colors in advance of the surgical procedure. The look-up table may be stored in a database (e.g., database 115 of FIG. 1A and/or database 247 of FIG. 2) for quick access to reduce the computational burden. The pre-computed estimated true colors each have a corresponding potential imaged color from the image sensor. For example, the pre-computed estimated true color may be determined from other surgical videos having a similar anatomical view of the surgical procedure. Thus, with the look-up table, the estimated true color for each of the plurality of pixels may be determined by comparing the imaged color of the first frame of the video to the corresponding potential imaged color of the pre-computed estimated true colors. Interpolation can then be utilized to estimate the estimated true color based, at least in part, on the pre-computed estimated true colors of the look-up table and the imaged color.

It is appreciated that in some embodiments, the individual steps of method 300 may be performed at different times before, during, or after the surgical procedure. For example, steps 302, 304, 306, and 308 may be performed before the surgical procedure occurs. Steps 310 and 312 may be performed during the surgical procedure or before the surgical procedure. For example, the look-up table may be generated before the surgical procedure occurs. Step 314 may be performed during the surgical procedure. In other embodiments, with the availability of enough computation power, it is possible to perform the entirety of method 300 during the surgical procedure. In this embodiment, steps 302, 304, 306, and 308 may be performed incrementally such that the entire video database is not processed multiple times during the surgical procedure. In other embodiments, method 300 may be utilized to desmoke a video of the surgical procedure from a surgical video database or the like.

Figure 4:
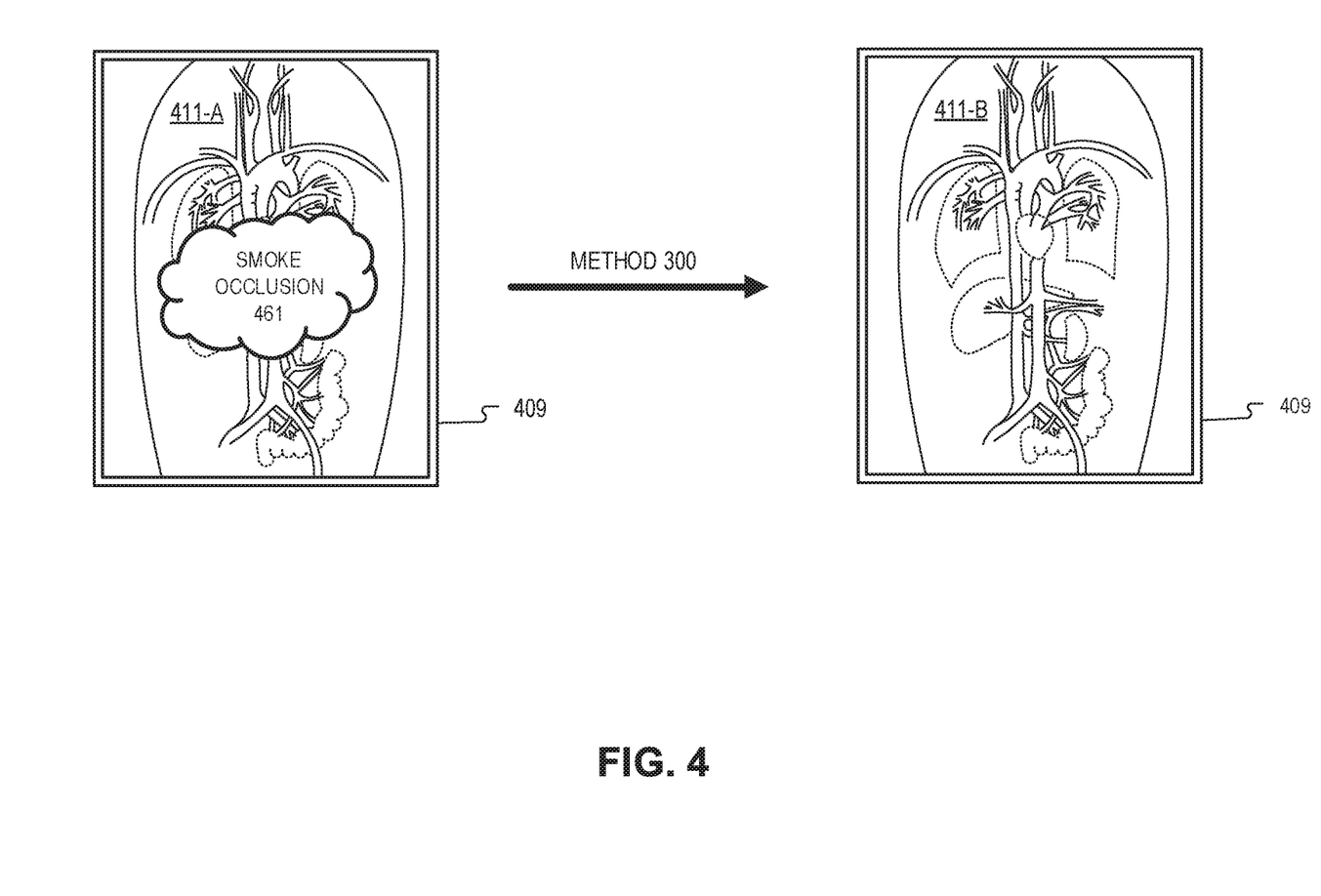
FIG. 4 is an example display screen of a surgical system receiving an image affected by a smoke occlusion and outputting a desmoked image with reduced smoke occlusion in real-time, in accordance with an embodiment of the disclosure.

FIG. 4 is an example display screen 409 of a surgical system (e.g., surgical system 100-A of FIG. 1A) receiving an image 411-A (e.g., the first image frame) affected by the smoke occlusion and outputting the desmoked image 411-B (e.g., the desmoked first image frame) with reduced smoke occlusion in real-time, in accordance with an embodiment of the disclosure. Without the application of method 300, display screen 409 would output image 411-A, which illustrates smoke occlusion 461 at least partially obstructing the surgeon's view of the surgical site. However, with the application of method 300, desmoked image 411-B is generated by determining the estimated true color of each of the plurality of pixels in image 411-A. Thus, display screen 409 outputs desmoked image 411-B with the reduced amount of the smoke occlusion relative to image 411-A.

Figure 5A:
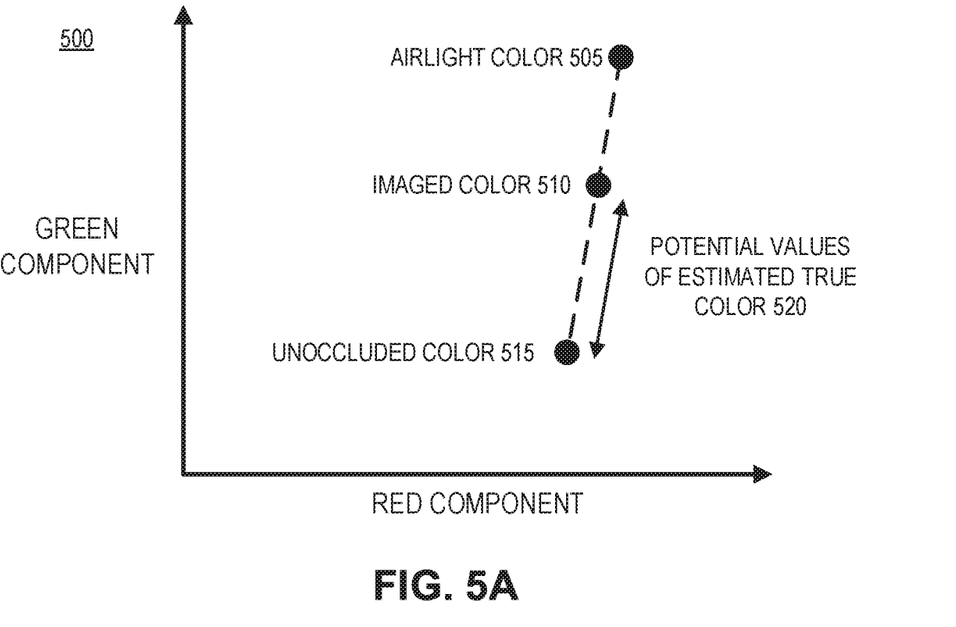
FIGS. 5A and 5B are graphical representations of red color and green color components of a pixel of an image frame affected by a smoke occlusion.
Figure 5B:
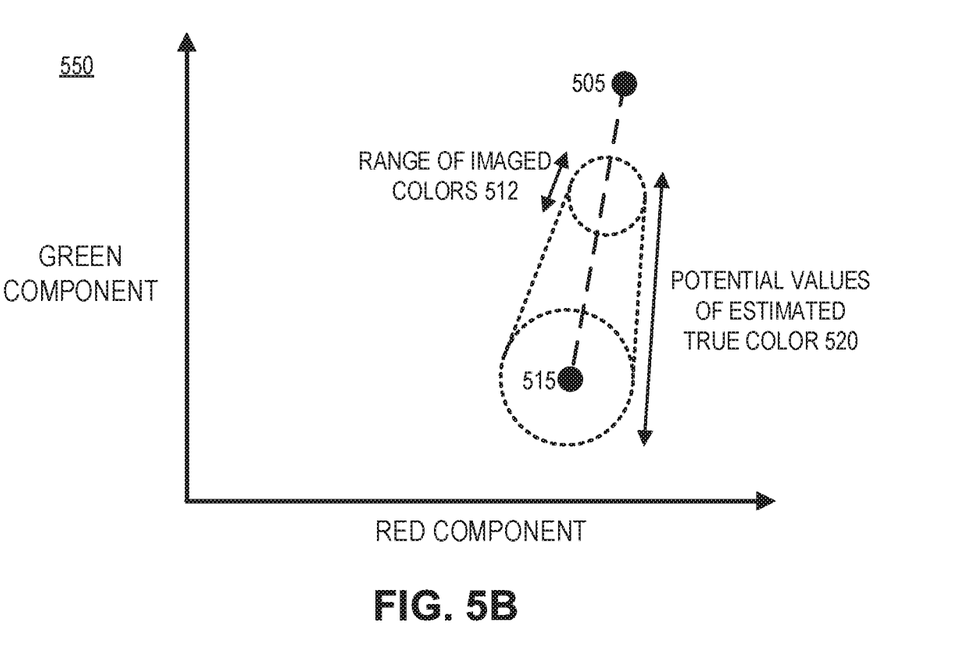

FIGS. 5A and 5B are graphical representations of the red color component and the green color component of a first pixel included in the plurality of pixels of the first image frame. While only the red color component and the green color components are illustrated, it is appreciated that the same graphical representations may be illustrated with the blue color component value in conjunction with either or both the red color component and the green color component.

As illustrated in FIG. 5A, it is assumed that imaged color 510 is a discrete value determined by the image sensor. Thus, based on the location of the airlight color 505 (e.g., the color value of the surgical smoke that is dense enough to form a smoke occlusion that is opaque), imaged color 510 of the tissue determined/senses by an image sensor, and unoccluded color 515 (e.g. the true color or actual color) of the tissue unaffected by the smoke occlusion, the estimated true color may be determined. As depicted, the estimated true color lies within a range of potential values of estimated true color 520, in accordance of embodiments of the disclosure.

However, it is appreciated that the imaged color 510 may not be a discrete value, but rather, may be range of imaged colors 512 as illustrated in FIG. 5B due to noise from the image sensor. The range of imaged colors 512 may be represented as sphere to simplify the numerical calculations for determining the estimated true color while also compensating for the noise. Thus, the range of imaged colors 512 may lead to a larger range of potential values of estimated true color 520. The estimated true color C(x) may then be determined by adjusting Equation 2 and Equation 3 to compensate for the noise. If the transmittance values is t then the unoccluded color 515 (e.g., estimated true color of the tissue if the smoke occlusion were absent) can be re-written as a sphere with radius of 1/t:

$$\frac{1}{t}S(x) - \left(1 - \frac{1}{t}\right)A. \quad (5)$$

Now the integrand in the numerator and the denominator of Equation 3, along with the limits can be replaced as follows to compensate for the noise:

$$\frac{\int_{D\left(\left(\frac{1}{t}\right)S+\left(1-\frac{1}{t}\right)A, ut\right)} tq(t)p\left(\frac{S_r - (1-t)A_r}{t}, \ldots\right) dxdydz}{\int_{D\left(\left(\frac{1}{t}\right)S+\left(1-\frac{1}{t}\right)A, ut\right)} q(t)p\left(\frac{S_r - (1-t)A_r}{t}, \ldots\right) dxdydz}, \quad (6)$$

where D(p, r) is the region inside the sphere at center p and radius r. Numerically integrating Equation 6 yields an estimated true color value of each of the plurality of pixels that compensates for the noise of the image sensor, in accordance of embodiments of the disclosure.

In other embodiments, it is appreciated that instead of estimating the expected transmittance value and then using the expected transmittance value to estimate the estimated true color, the estimated true color may be estimated directly. In yet other embodiments, it is appreciated that in-situ Bayesian inference (e.g., during the surgical procedure) may also be utilized. In other words, the first probability distribution, the second probability distribution, and the conditional probability distribution may be updated with each image frame (including the first image frame) of the video. Thus, embodiments of the disclosure may progressively improve in accuracy of estimating the true color as the surgical procedure progresses. It is further appreciated that while embodiments of the disclosure are discussed in reference to the plurality of pixels affected by the smoke occlusion, that the systems and methods of the disclosure may also be utilized on other pixels unaffected by the smoke occlusion. However, the imaged color of the other pixels would be substantially similar to the true color, and thus the estimated true color may be substantially similar to the imaged color. Therefore, it may not be necessary to identify that one of the pixels of the plurality of pixels is actually affected by the smoke occlusion.

The processes explained above are described in terms of computer software and hardware. The techniques described may constitute machine-executable instructions embodied within a tangible or non-transitory machine (e.g., computer) readable storage medium, that when executed by a machine (e.g., controller 107) will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for improving imaging during a surgical procedure, comprising:
    an image sensor configured to capture a video of the surgical procedure, wherein the video includes a first image frame with a smoke occlusion due to surgical smoke, and wherein the first image frame includes a plurality of pixels each having an imaged color representing a view of tissue affected by the smoke occlusion; and
    a controller coupled to the image sensor to receive the video, wherein the controller stores instructions that when executed by the controller causes the system to perform operations including:

determining an estimated true color of each of the plurality of pixels in the first image frame based, at least in part, on the imaged color, wherein the estimated true color is closer to an unoccluded color of the tissue than the imaged color, wherein determining the estimated true color of each of the plurality of pixels includes:
determining a conditional probability distribution of transmittance values of the smoke occlusion for each of the plurality of pixels; and
generating, in response to determining the estimated true color, a desmoked first image frame with a reduced amount of the smoke occlusion relative to the first image frame.

2. The system of claim 1, further comprising a display screen coupled to display a desmoked video, including the desmoked first image frame, in real-time while capturing the video with the image sensor.

3. The system of claim 1, wherein the image sensor is included in at least one of a system for robotic surgery or an endoscope system.

4. The system of claim 1, wherein
the conditional probability distribution of transmittance values of the smoke occlusion for each of the plurality of pixels is based, at least in part, on the imaged color, a first probability distribution of potential true colors of the tissue, and a second probability distribution of potential transmittance values of the smoke occlusion.

5. The system of claim 4, wherein determining the estimated true color of each of the plurality of pixels includes:
determining an expected transmittance value of the smoke occlusion for each of the plurality of pixels based, at least in part, on the conditional probability distribution of the transmittance values; and
estimating, in response to determining the expected transmittance value, the estimated true color based, at least in part, on the imaged color and the expected transmittance value of the smoke occlusion.

6. The system of claim 4, further comprising:
a cauterizing instrument coupled to the controller, and wherein the controller includes further instructions that when executed by the controller causes the system to perform further operations including:
monitoring an activation of the cauterizing instrument to detect a cauterization event; and
in response to detecting the cauterization event, adjusting the conditional probability distribution of the transmittance values of the smoke occlusion to compensate for an increased likelihood the smoke occlusion is affecting the imaged color.

7. The system of claim 4, further comprising:
a surgical video database coupled to the controller, wherein the surgical video database includes a plurality of smoke-free images representing the surgical procedure without the smoke occlusion at a substantially similar anatomical location as the first image frame, and
wherein the controller includes further instructions that when executed by the controller causes the system to perform further operations including:
determining the first probability distribution of the potential true colors of the tissue based, at least in part, on the plurality of smoke-free images.

8. The system of claim 4, wherein the imaged color is a range of imaged colors due to noise from the image sensor, and wherein the conditional probability distribution of the transmittance values based, at least in part, on the range of imaged colors to compensate for the noise.

9. The system of claim 4, further comprising:
an input apparatus coupled to the controller, the input apparatus to receive an input command from an operator of the system, and wherein the controller includes further instructions that when executed by the controller causes the system to perform further operations including:
in response to receiving the input command, adjusting a level of the reduced amount of the smoke occlusion relative to the first image frame.

10. The system of claim 1, further comprising:
a database coupled to the controller, wherein the database includes a look-up table having pre-computed estimated true colors, wherein each of the pre-computed estimated true colors have a corresponding potential imaged color of the image sensor, and wherein determining the estimated true color of each of the plurality of pixels includes:
comparing the imaged color of the video to the corresponding potential imaged color of the pre-computed estimated true colors; and
estimating, in response to comparing the imaged color, the estimated true color based, at least in part, on the pre-computed estimated true colors of the look-up table.

11. The system of claim 10, wherein estimating the estimated image color includes:
interpolating the estimated true color from the lookup table based on the imaged color.

12. A method for reducing a smoke occlusion in a surgical video, comprising:
receiving a plurality of image frames corresponding to the surgical video of a surgical procedure, wherein the plurality of image frames includes a first image frame with the smoke occlusion due to surgical smoke, and wherein the first image frame includes a plurality of pixels each having an imaged color representing a view of tissue affected by the smoke occlusion;
determining an estimated true color of each of the plurality of pixels in the first image frame based, at least in part, on the imaged color, wherein the estimated true color is closer to an unoccluded color of the tissue than the imaged color, wherein determining the estimated true color of each of the plurality of pixels includes:
determining a conditional probability distribution of transmittance values of the smoke occlusion for each of the plurality of pixels; and
generating, in response to determining the estimated true color, a desmoked video, including a desmoked first image frame with a reduced amount of the smoke occlusion relative to the first image frame.

13. The method of claim 12, further comprising outputting the desmoked video image to a display screen in real-time while receiving the plurality of image frames.

14. The method of claim 12, further comprising, in response to input from an operator, adjusting a level of the reduced amount of the smoke occlusion.

15. The method of claim 12, further comprising:
capturing the plurality of image frames with an image sensor disposed in at least one of an endoscope or a surgical robot, wherein the image sensor is coupled to the processor, and wherein the processor receives the plurality of images from the image sensor.

16. The method of claim 12, wherein
the conditional probability distribution of transmittance values of the smoke occlusion for each of the plurality of pixels is based, at least in part, on the imaged color, a first probability distribution of potential true colors of the tissue, and a second probability distribution of potential transmittance values of the smoke occlusion.

17. The method of claim 16, wherein determining the estimated true color of each of the plurality of pixels includes:
determining an expected transmittance value of the smoke occlusion for each of the plurality of pixels based, at least in part, on the conditional probability distribution of the transmittance values; and
estimating, in response to determining the expected transmittance value, the estimated true color based, at least in part, on the imaged color and the transmittance value of the smoke occlusion.

18. The method of claim 16, wherein the imaged color is a range of imaged colors due to image sensor noise, and wherein the conditional probability distribution of the transmittance values based, at least in part, on the range of imaged colors to compensate for the image sensor noise.

19. The method of claim 16, further comprising:
receiving a plurality of smoke-free images representing the surgical procedure without the smoke occlusion at a substantially similar anatomical location as the first image frame; and
determining the first probability distribution of the potential true colors of the tissue, based, at least in part, on the plurality of smoke-free images.

20. The method of claim 12, wherein determining the estimated true color of each of the plurality of pixels includes:
receiving a look-up table having pre-computed estimated true colors, wherein each of the pre-computed estimated true colors have a corresponding potential imaged color;
comparing the imaged color of the first image frame to the corresponding potential imaged color of the pre-computed estimated true colors;
estimating, in response to comparing the imaged color, the estimated true color by interpolation of the look-up table based, at least in part, on the pre-computed estimated true colors, the corresponding potential imaged color, and the imaged color.

21. A system for improving imaging during a surgical procedure, comprising:
an image sensor configured to capture a video of the surgical procedure, wherein the video includes a first image frame with a smoke occlusion due to surgical smoke, and wherein the first image frame includes a plurality of pixels each having an imaged color representing a view of tissue affected by the smoke occlusion;
a database including a look-up table having pre-computed estimated true colors, wherein each of the pre-computed estimated true colors have a corresponding potential imaged color of the image sensor; and
a controller coupled to the database and the image sensor to receive the video, wherein the controller stores instructions that when executed by the controller causes the system to perform operations including:
determining an estimated true color of each of the plurality of pixels in the first image frame based, at least in part, on the imaged color, wherein the estimated true color is closer to an unoccluded color of the tissue than the imaged color, wherein determining the estimated true color of each of the plurality of pixels includes:
comparing the imaged color of the video to the corresponding potential imaged color of the pre-computed estimated true colors; and
estimating, in response to comparing the imaged color, the estimated true color based, at least in part, on the pre-computed estimated true colors of the look-up table; and
generating, in response to determining the estimated true color, a desmoked first image frame with a reduced amount of the smoke occlusion relative to the first image frame.

22. A non-transitory machine readable storage medium having instructions stored thereon, which, when executed by one or more processors, cause the one or more processors to perform a method comprising:
receiving a plurality of image frames corresponding to a surgical video of a surgical procedure, wherein the plurality of image frames includes a first image frame with a smoke occlusion due to surgical smoke, and wherein the first image frame includes a plurality of pixels each having an imaged color representing a view of tissue affected by the smoke occlusion;
determining an estimated true color of each of the plurality of pixels in the first image frame based, at least in part, on the imaged color, wherein the estimated true color is closer to an unoccluded color of the tissue than the imaged color, wherein determining the estimated true color of each of the plurality of pixels includes:
receiving a look-up table having pre-computed estimated true colors, wherein each of the pre-computed estimated true colors have a corresponding potential imaged color;
comparing the imaged color of the first image frame to the corresponding potential imaged color of the pre-computed estimated true colors; and
estimating, in response to comparing the imaged color, the estimated true color by interpolation of the look-up table based, at least in part, on the pre-computed estimated true colors, the corresponding potential imaged color, and the imaged color; and
generating, in response to determining the estimated true color, a desmoked video, including a desmoked first image frame with a reduced amount of the smoke occlusion relative to the first image frame.

* * * * *